(12) United States Patent
Jung

(10) Patent No.: US 10,748,662 B2
(45) Date of Patent: Aug. 18, 2020

(54) CONTENT-BASED MEDICAL IMAGE RETRIEVAL METHOD AND RETRIEVAL SYSTEM

(71) Applicant: Vuno, Inc., Seoul (KR)

(72) Inventor: Kyu Hwan Jung, Seoul (KR)

(73) Assignee: Vuno, Inc., Seoul (KR)

( * ) Notice: Subject to any disclaimer, the term of this patent is extended or adjusted under 35 U.S.C. 154(b) by 198 days.

(21) Appl. No.: 15/949,537

(22) Filed: Apr. 10, 2018

(65) Prior Publication Data

US 2019/0066847 A1 Feb. 28, 2019

(51) Int. Cl.
*G16H 50/70* (2018.01)
*G06T 7/11* (2017.01)
(Continued)

(52) U.S. Cl.
CPC ......... *G16H 50/70* (2018.01); *G06K 9/00201* (2013.01); *G06K 9/627* (2013.01); *G06N 3/0445* (2013.01); *G06N 3/08* (2013.01); *G06T 7/0012* (2013.01); *G06T 7/0014* (2013.01); *G06T 7/11* (2017.01); *G06T 7/143* (2017.01); *G06T 15/08* (2013.01); *G16H 30/20* (2018.01);
(Continued)

(58) Field of Classification Search
CPC ........ G16H 50/70; G16H 30/20; G16H 50/20; G16H 30/40; G06T 7/143; G06T 7/11; G06T 7/0012; G06T 7/0014; G06T 15/08; G06K 9/00201; G06K 9/627; G06N 3/0445; G06N 3/08
See application file for complete search history.

(56) References Cited

U.S. PATENT DOCUMENTS

| 10,262,226 B1* | 4/2019 | Flowers | G06K 9/00201 |
| 2004/0086162 A1* | 5/2004 | Doi | G06T 7/0012 |
| | | | 382/131 |

(Continued)

FOREIGN PATENT DOCUMENTS

| KR | 10-1431745 | 8/2014 |
| KR | 10-1443187 | 9/2014 |
| KR | 10-2017-0046104 | 4/2017 |

OTHER PUBLICATIONS

Google Scholar Search Results.*
Chen, Jianxu, et al. "Combining fully convolutional and recurrent neural networks for 3d biomedical image segmentation." Advances in Neural Information Processing Systems. 2016.
Donahue, Jeffrey, et al. "Long-term recurrent convolutional networks for visual recognition and description." Proceedings of the IEEE conference on computer vision and pattern recognition. 2015.

*Primary Examiner* — Qun Shen
(74) *Attorney, Agent, or Firm* — IP & T Group LLP

(57) ABSTRACT

A content-based medical image retrieval method and a retrieval system using the same include: obtaining m (2≤m≤n) number of unit images from a three-dimensional (3D) medical image including n (n≥2) number of unit images and extracting features per unit image from each of the m (2≤m≤n) number of unit images through a feature extraction unit, wherein the 3D medical image is voxel data including a plurality of slices and each of the plurality of slices is defined as a unit image; inputting features of each unit image extracted from the m (2≤m≤n) number of unit images to a recurrent neural network to generate an output value; and performing medical image retrieval using the output value through an input processing unit, wherein a plurality of 3D medical images to be compared with the output value include a 3D medical image having p (p≥2, p≠n) number of unit images.

7 Claims, 9 Drawing Sheets

(51) Int. Cl.
*G06T 7/00* (2017.01)
*G06T 15/08* (2011.01)
*G16H 30/40* (2018.01)
*G06N 3/04* (2006.01)
*G06N 3/08* (2006.01)
*G06K 9/62* (2006.01)
*G16H 50/20* (2018.01)
*G06K 9/00* (2006.01)
*G06T 7/143* (2017.01)
*G16H 30/20* (2018.01)

(52) U.S. Cl.
CPC .............. *G16H 30/40* (2018.01); *G16H 50/20* (2018.01); *G06K 2209/05* (2013.01); *G06T 2200/24* (2013.01); *G06T 2207/10081* (2013.01); *G06T 2207/20081* (2013.01); *G06T 2207/20084* (2013.01); *G06T 2207/30061* (2013.01); *G06T 2207/30064* (2013.01); *G06T 2210/41* (2013.01)

(56) References Cited

U.S. PATENT DOCUMENTS

| | | | |
|---|---|---|---|
| 2008/0009706 A1* | 1/2008 | Theriault | A61B 5/055 600/410 |
| 2009/0003676 A1* | 1/2009 | Li | G06T 7/12 382/131 |
| 2012/0283574 A1* | 11/2012 | Park | G06K 9/46 600/476 |
| 2015/0242704 A1* | 8/2015 | Nobori | G09G 3/002 345/589 |
| 2016/0307071 A1* | 10/2016 | Perronnin | G06K 9/66 |
| 2017/0039357 A1* | 2/2017 | Hwang | G06K 9/6293 |
| 2017/0294000 A1* | 10/2017 | Shen | G06T 11/001 |
| 2018/0082443 A1* | 3/2018 | Risman | G06T 7/0012 |
| 2018/0144466 A1* | 5/2018 | Hsieh | G06F 19/00 |
| 2019/0205606 A1* | 7/2019 | Zhou | G06N 3/0445 |
| 2019/0340751 A1* | 11/2019 | Kim | A61B 5/163 |

* cited by examiner

CONTENT-BASED MEDICAL IMAGE RETRIEVAL METHOD AND RETRIEVAL SYSTEM

CROSS REFERENCE TO RELATED APPLICATION

This application claims priority to and incorporates herein by reference all disclosure in Korean patent application no. 2017-0132872 filed Aug. 29, 2017.

TECHNICAL FIELD

The present disclosure relates to a content-based medical image retrieval method and a corresponding retrieval system, and more particularly, to a content-based medical image retrieval method and a corresponding retrieval system using a machine learning technique. Here, the content-based medical image retrieval method refers to a method of automatically extracting data-based attributes along with color, texture, shape, and existing features from a given medical image (e.g., 2D X-ray, CT image, MRI, PET image, etc.) and retrieving similar cases based on the extracted data-based attributes, unlike a conventional keyword-based (e.g., lung cancer) medical image retrieval method.

BACKGROUND ART

This section provides background information related to the present disclosure which is not necessarily prior art.

FIG. 1 is a diagram illustrating an example of a conventional method of segmenting a three-dimensional (3D) medical image using deep learning, in which a segmentation system includes n number of segmentation modules S1, ... Sj, ..., Sn, corresponding to n number of slices 1, ..., j, ..., n, a recurrent neural network (RNN) module R, and a segmentation probability map A for providing an integrated segmentation image. The 3D medical image is voxel data (e.g., CT image) including a plurality of slices, and in order to segment a target region such as a nodule from the 3D medical image, (1) a portion corresponding to a target region is segmented from each slice using a deep learning technique such as fully convolutional network (FCN) and the segmented portions are integrated, or (2) a 3D convolution may directly be used. In FIG. 1, a technique of performing segmentation on n number of slices 1, ..., n using a variant of U-net and utilizing an RNN (Recurrent Neural Network) such as an LSTM (Long Short-Term Memory network) to utilize spatial information between slices, rather than directly integrating the segmented slices, is illustrated (Combining Fully Convolutional and Recurrent Neural Networks for 3D Biomedical Image Segmentation; Jianxu Chen, Lin Yang, Yizhe Zhang, Mark Alber, Danny Z. Chen (Submitted on 5 Sep. 2016 (v1), last revised 6 Sep. 2016 (this version, v2)); arXiv.org>cs>arXiv:1609.01006).

FIG. 2 is a diagram illustrating an example of a conventional method of extracting features from a plurality of video frames using deep learning, in which a semantic extraction system includes a feature extraction unit F and a sequence learning unit SL. As an input X of the system, a plurality of video frames having time series characteristics may be used. The system may extract features from each of a plurality of video frames through the feature extraction unit F (e.g., convolutional neural network (CNN)) and then allow these features to pass through the sequence learning unit (e.g., LSTM), thereby extracting features or a meaning having time series characteristics as an output Y from the video (Long-term Recurrent Convolutional Networks for Visual Recognition and Description; Jeff Donahue, Lisa Anne Hendricks, Marcus Rohrbach, Subhashini Venugopalan, Sergio Guadarrama, Kate Saenko, Trevor Darrell; (Submitted on 17 Nov. 2014 (v1), last revised 31 May 2016 (this version, v4)); arXiv.org>cs>arXiv:1411.4389).

INVENTION

Technical Problem

It is, therefore, an object of the present disclosure to provide a content-based medical image retrieval method and a retrieval system using a machine learning technique.

Technical Solution

This section provides a general summary of the disclosure and is not a comprehensive disclosure of its full scope or all of its features.

According to one aspect of the present disclosure, there is provided a content-based medical image retrieval method, including: obtaining m ($2 \leq m \leq n$) number of unit images from a three-dimensional (3D) medical image including n ($n \geq 2$) number of unit images and extracting features per unit image from each of the m ($2 \leq m \leq n$) number of unit images through a feature extraction unit, wherein the 3D medical image is voxel data including a plurality of slices and each of the plurality of slices is defined as a unit image; inputting features of each unit image extracted from the m ($2 \leq m \leq n$) number of unit images to a recurrent neural network to generate an output value; and performing medical image retrieval using the output value through an input processing unit, wherein a plurality of 3D medical images to be compared with the output value include a 3D medical image having p ($p \geq 2$, $p \neq n$) number of unit images.

According to another aspect of the present disclosure, there is provided a content-based medical image retrieval system between a user interface and a medical image storage unit, including: a learning unit which learns using a three-dimensional (3D) medical image provided from a medical image storage unit as training data, and receives the 3D medical image and derives an output value, wherein the 3D medical image is voxel data including a plurality of slices and each of the plurality of slices is defined as a unit image, and the learning unit includes a feature extraction unit for obtaining a plurality of unit images from the 3D medical image and extracting features per unit image from each of the unit images and a recurrent neural network for receiving the features of each unit image to generate an output value; a user interface side output value processing unit for receiving the medical images provided from the user interface to derive an output value; and an input processing unit, as a storage space for storing the output value from the learning unit, for deriving an output value of at least one learning unit corresponding to the output value of the user interface side output value processing unit.

Advantageous Effects

According to a content-based medical image retrieval method and system of the present disclosure, it is possible to provide a content-based medical image retrieval method and a retrieval system that can be performed without any problem even when the number of unit images constituting each of the plurality of medical images is different.

DESCRIPTION OF DRAWINGS

The above and other objects and features of the present disclosure will become apparent from the following description of embodiments, given in conjunction with the accompanying drawings, in which.

BEST MODE

Hereinafter, embodiments of the present disclosure will be described in detail with the accompanying drawings.

Figure 1:
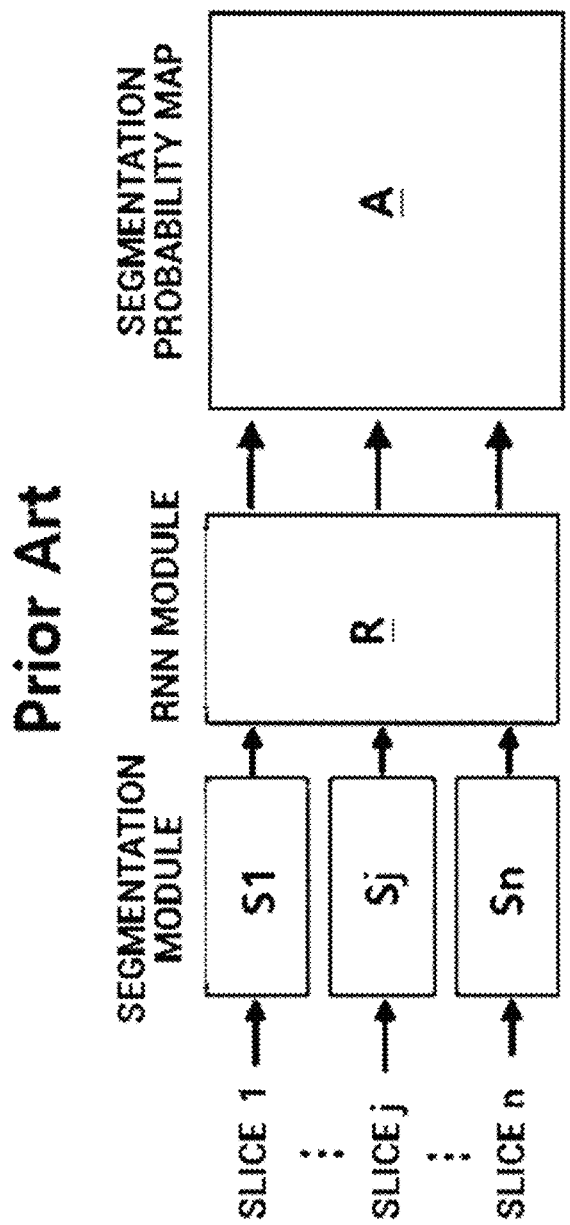
FIG. 1 is a diagram illustrating an example of a conventional method of segmenting a 3D medical image using deep learning.
Figure 2:
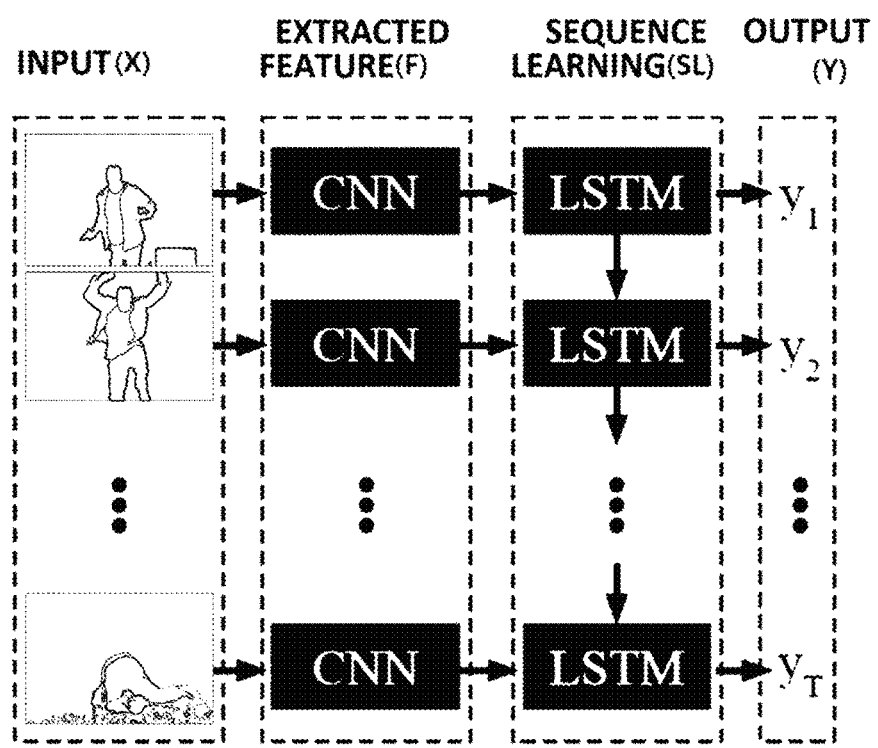
FIG. 2 is a diagram illustrating an example of a conventional method of extracting features from a plurality of video frames using deep running.
Figure 3:
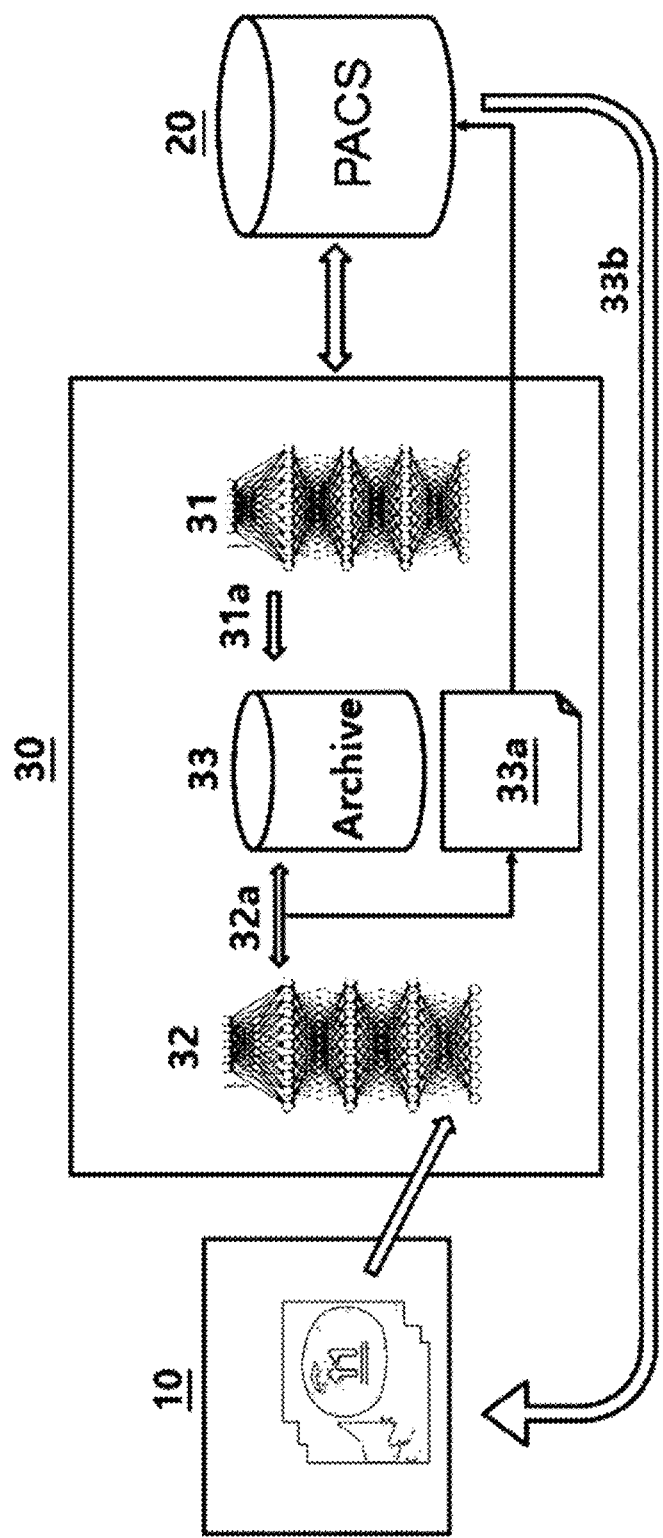
FIG. 3 is a diagram illustrating an example of a content-based medical image retrieval system according to the present disclosure.

FIG. 3 is a diagram illustrating an example of a content-based medical image retrieval system according to the present disclosure, in which the system includes a user interface 10, a medical image storage unit 20, and a retrieval module or system 30.

The user interface 10 is means for inputting a medical image 11 desired to be retrieved by a user (e.g., doctor) or an output value already obtained by processing the medical image 11 to the retrieval module or system 20. A typical example of the user interface 10 may be a personal computer (PC), a smartphone or the like, and may be connected to the retrieval module or system 30 via a network wirelessly or wiredly.

The medical image storage unit 20 may store a plurality of medical images and provide the plurality of stored medical images so that the search module or system 30 may use the medical images in learning. The medical image storage unit 20 may be simply a memory space or a DB (database), or may be a system which may store and retrieve a medical image, like a picture archiving and communication system (PACS). The plurality of medical images include two-dimensional (2D) medical images (e.g., x-ray images) and/or 3D medical images (e.g., CT images, MRI, PET images) and are not particularly limited as long as they are medical images.

The retrieval module or system 30 (retrieval means) includes a learning unit 31, a user interface side output value processing unit 32, and an input processing unit 33. The learning unit 31 is a learning module or system which is trained using a plurality of medical images provided from the medical image storage unit 20, as training data. When completed in the training, the learning unit 31 receives each of the plurality of medical images stored in the medical image storage unit 20, derives an output value 31a therefrom, and provides the output value 31a to the input processing unit 33 (see FIG. 5). The user interface side output value processing unit 32 may have the same form as the trained learning unit 31, and receives the medical image 11 provided from the user interface 10 and derives an output value 32a therefrom. In the case where the user interface side output value processing unit 32 or the trained learning unit 31 is provided on the user interface 10 side, it is to be understood that the processed output value 32a, rather than the medical image 11, may be provided directly to the retrieval module or system 30. Meanwhile, in the case where the trained learning unit 31 and the user interface side output value processing unit 32 have the same form, it is to be understood that they may not need to be independently present within the retrieval module or system 30 and only any one of them may be present. The input processing unit 33 is a storage space which stores the output value 31a regarding each of the plurality of medical images provided from the learning unit 31 and is means which derives at least one output value 31a corresponding to the output value 32a from the storage space using the output value 32a. For example, the input processing unit 33 may have a form of archive, and is not limited thereto but may have any form as long as it supports to store a value and to retrieve a corresponding value. Here, for example, when the output value 32a and the output value 31a match, the values may have high similarity. When at least one corresponding output value 31a is derived, the retrieval module or system 30 may make a request 33a to the medical image storage unit 20 so that a corresponding medical image and/or patient information (medical history, disease name, etc.) attached to the medical image may be provided (as indicated by the arrow 33b) to the user interface 10. The content-based medical image retrieval system illustrated in FIG. 3 may be presented as an example, and in the present disclosure, any system may be used as long as it supports to derive the output value 32a from the medical image 11, to compare the derived output value 32a with the output value 31a which has been derived from each of the plurality of medical images and stored, and to provide the comparison result together with a corresponding medial image and/or patient information.

Figure 4:
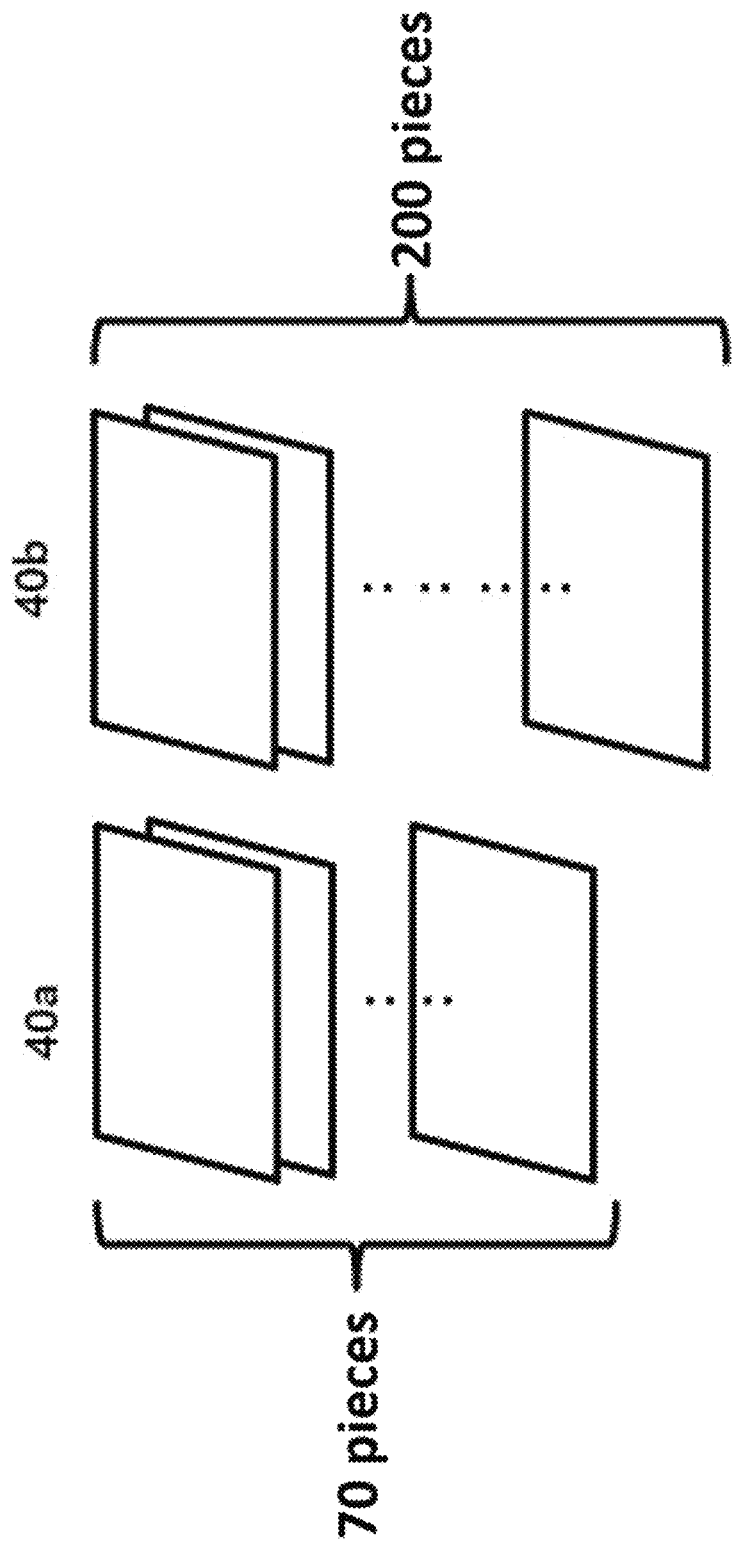
FIG. 4 is a diagram illustrating an example of medical image data that may be used in the content-based medical image retrieval system according to the present disclosure.

FIG. 4 is a diagram illustrating an example of medical image data that may be used in the content-based medical image retrieval system according to the present disclosure, in which the medical image 40a or 40b (e.g., CT image) may include a plurality of slices (e.g., p (p≥2) number of slices), i.e., p number of unit images (1, ..., p), as voxel data. When the medical image 40a or 40b including the plurality of unit images 1, ..., p is used to train the learning unit 31, it may mean that at least some (q number of unit images (2≤q≤p)) of the unit images, among the p (p≥2) number of unit images 1, ..., p, are input as training data the learning unit 31. Here, a problem may arise in that a plurality of medical images, although they have the same modality, may be obtained through imaging devices made by different makers, so that the number of the entire slices, i.e., the number of the entire unit images, may not be the same due to several reasons. For example, a CT image 40a may have 70 unit images in an axial direction, while another CT image 40b may have 200 unit images. The present disclosure is to provide a content-based medical image retrieval method and system which may be carried out without any problem although the numbers of unit images respectively constituting a plurality of medical images are different.

Figure 5:
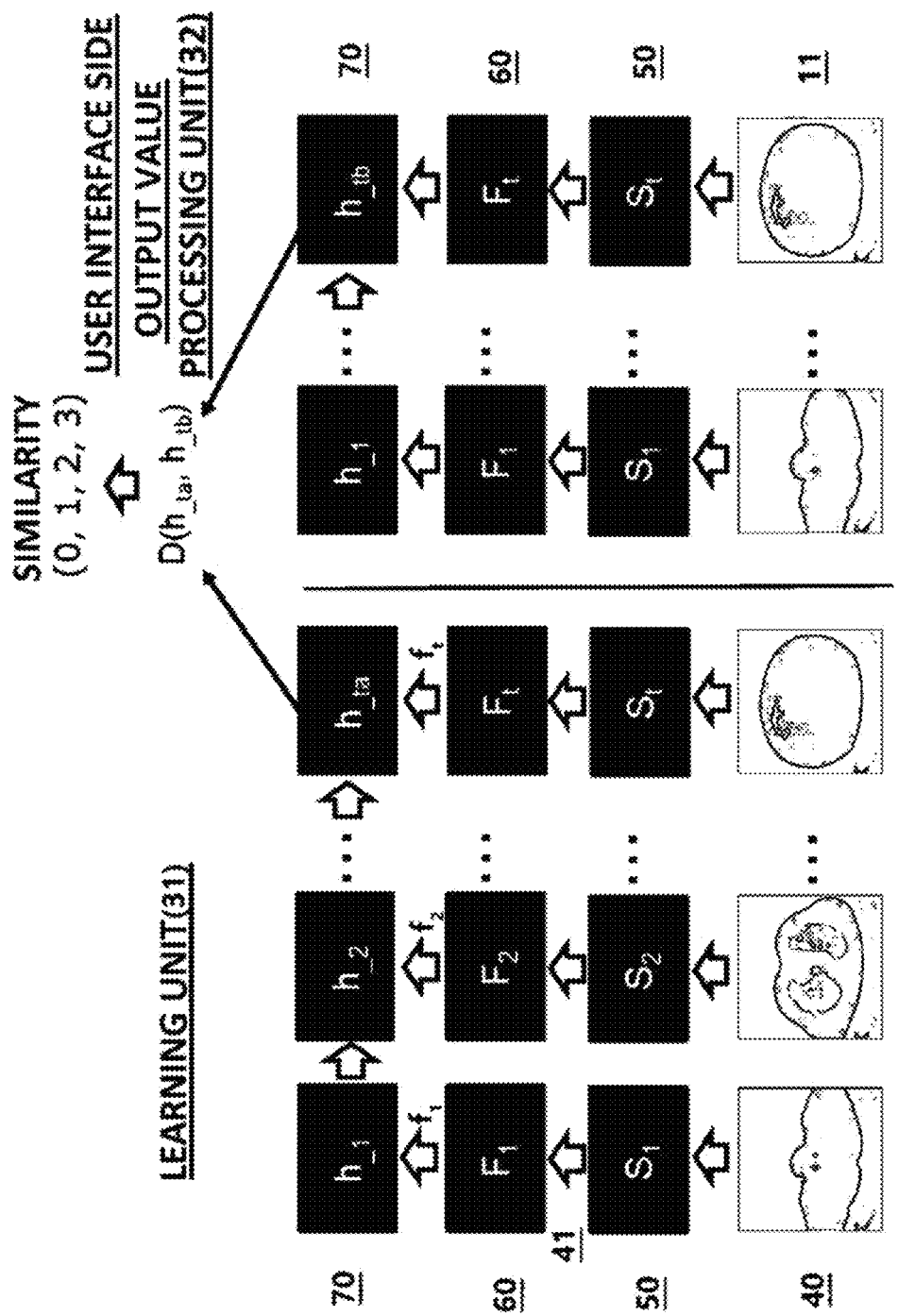
FIG. 5 is a diagram illustrating an example of a learning unit or a user interface side output value processing unit according to the present disclosure.

FIG. 5 is a diagram illustrating an example of the learning unit or the user interface side output value processing unit according to the present disclosure. Training is performed using a medical image 40 in the learning unit 31, and a plurality of medical images 40 are used for training. When the learning is completed, an output value $H_{\_ta}$ is derived for the plurality of medical images 40 and the output value $H_{\_ta}$ is stored. The plurality of medical images 40 used for deriving the output value $H_{\_ta}$ may be the same as the medical image 40 used for training but may also include a medical image different from the medical image 40 used for training. Similarly, an output value $H_{\_tb}$ is derived from the medical image 11 in the user interface side output value processing unit 32 having the same form. The output value $H_{\_tb}$ and the output value $H_{\_ta}$ may be compared to determine similarities 0, 1, 2, and 3. For example, a function D ($H_{\_ta}, H_{\_ta}$) for calculating a distance between the output values ($H_{\_ta}, H_{\_ta}$) may be used for comparison.

More specifically, the learning unit 31 includes a feature extraction unit 60 and a recurrent neural network 70. Preferably, the learning unit 31 further includes a segmentation module 50, in which the segmentation module 50 serves to segment a specific region from each of unit images constituting the medical image 40 (see FIGS. 6A and 6B). Prior to inputting the medical image 40 to the feature extraction unit 60, the specific region may be segmented using the segmentation module 50, whereby only the specific region may be processed in the feature extraction unit 60, increasing the accuracy and rate of feature extraction. The feature extraction unit 60 extracts features from the medical image 40 (see FIG. 7). The features thus extracted, rather than being directly compared with the features extracted from the medical image 11, may be processed in a comparable form through the recurrent neural network 70 and then compared with each other. This is because, in the case where the number of unit images constituting the medical image 40 and the number of unit images constituting the medical image 11 are different, direct comparison therebetween may degrade the accuracy. In the example illustrated in FIG. 5, the segmentation module 50 and the feature extraction unit 60 are each configured to receive t (t≥2) number of inputs, and thus, t (t≥2) number of unit images of the medical image 40, among the unit images of the medical image 40 including p (p≥2) number of unit images, may be used by a single input, and t (t≥2) number of unit images of the medical image 11, among the unit images of the medical image 11 including n (n≥2) number of unit images, may be used by a single input. In order to process t (t≥2) number of input unit images as an input, the segmentation module 50 may have t (t≥2) number of internal modules $S_1, \ldots, S_t$ and the feature extraction unit 60 may have t (t≥2) number of internal modules $F_1, \ldots, F_t$, whereby t (t≥2) number of features $f_1, \ldots, f_t$ per unit image may be extracted per unit image. The recurrent neural network 70 is configured to derive t (t≥2) number of status values $H_{\_1}, \ldots, H_{\_ta}$. The status value $H_{\_ta}$ corresponds to the output value $H_{\_ta}$, and similarly, the status value $H_{\_tb}$ corresponds to the output value $H_{\_tb}$. For example, the LSTM may be used as the recurrent neural network 70, and any network may be used as long as it can derive an outcome or a meaning using context between outputs from the feature extraction unit 60. The recurrent neural network 70 may be applied to an arbitrary number of time series vectors, and thus, the recurrent neural network 70 may be applied, regardless of the p (p≥2) number or the n (n≥2) number of unit images. However, if the p (p≥2) number or the n (n≥2) number is large (e.g., a CT image having 300 unit images), an amount of calculation is significantly increased, and thus, the unit images may be sampled at a specific interval (e.g., one unit image per 10 unit images) or randomly (spatial order must be preserved), and input.

Figure 6A:
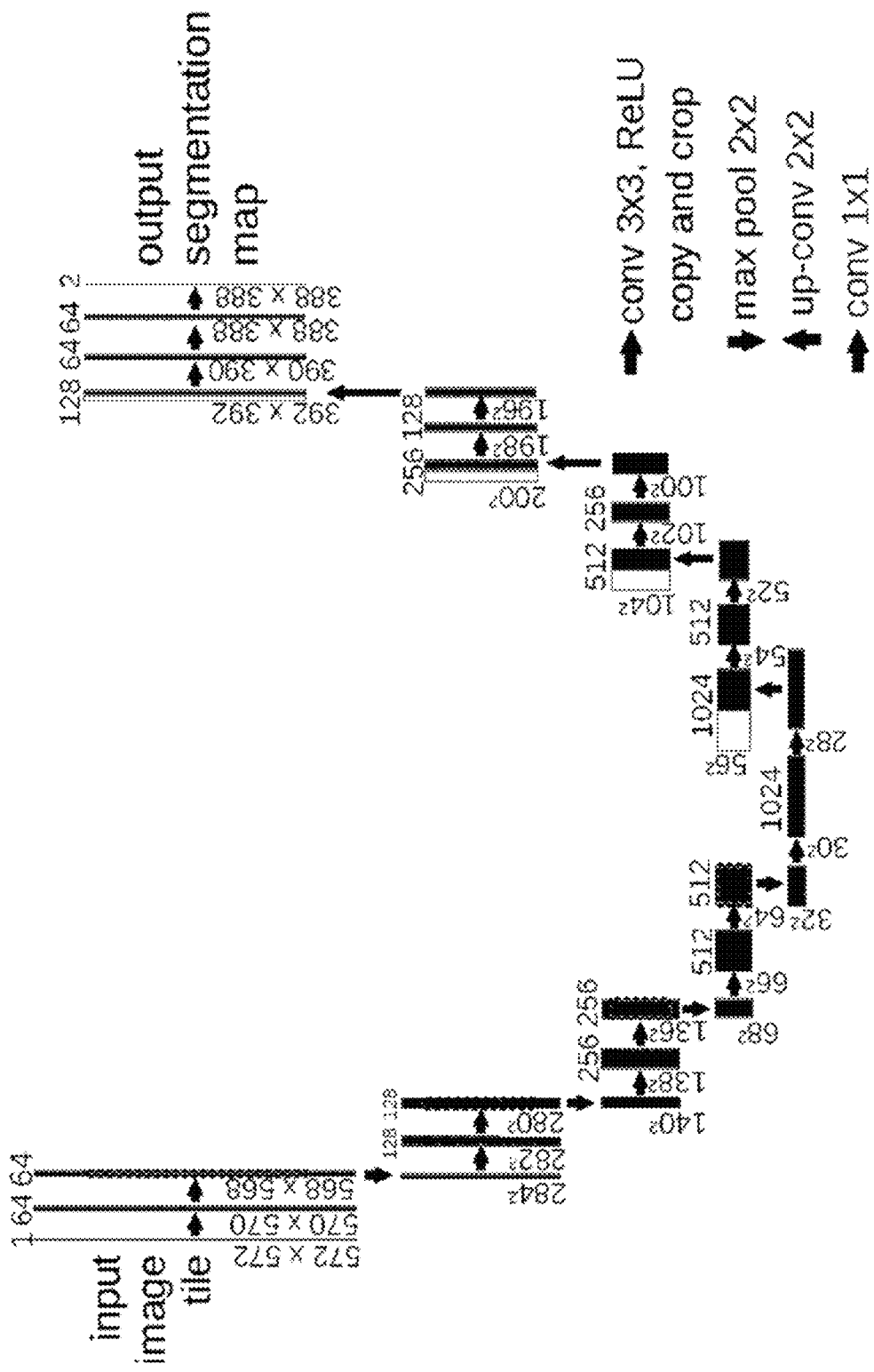
FIGS. 6A and 6B are views illustrating an example of a process of segmenting a specific region from a medical image according to the present disclosure.
Figure 6B:
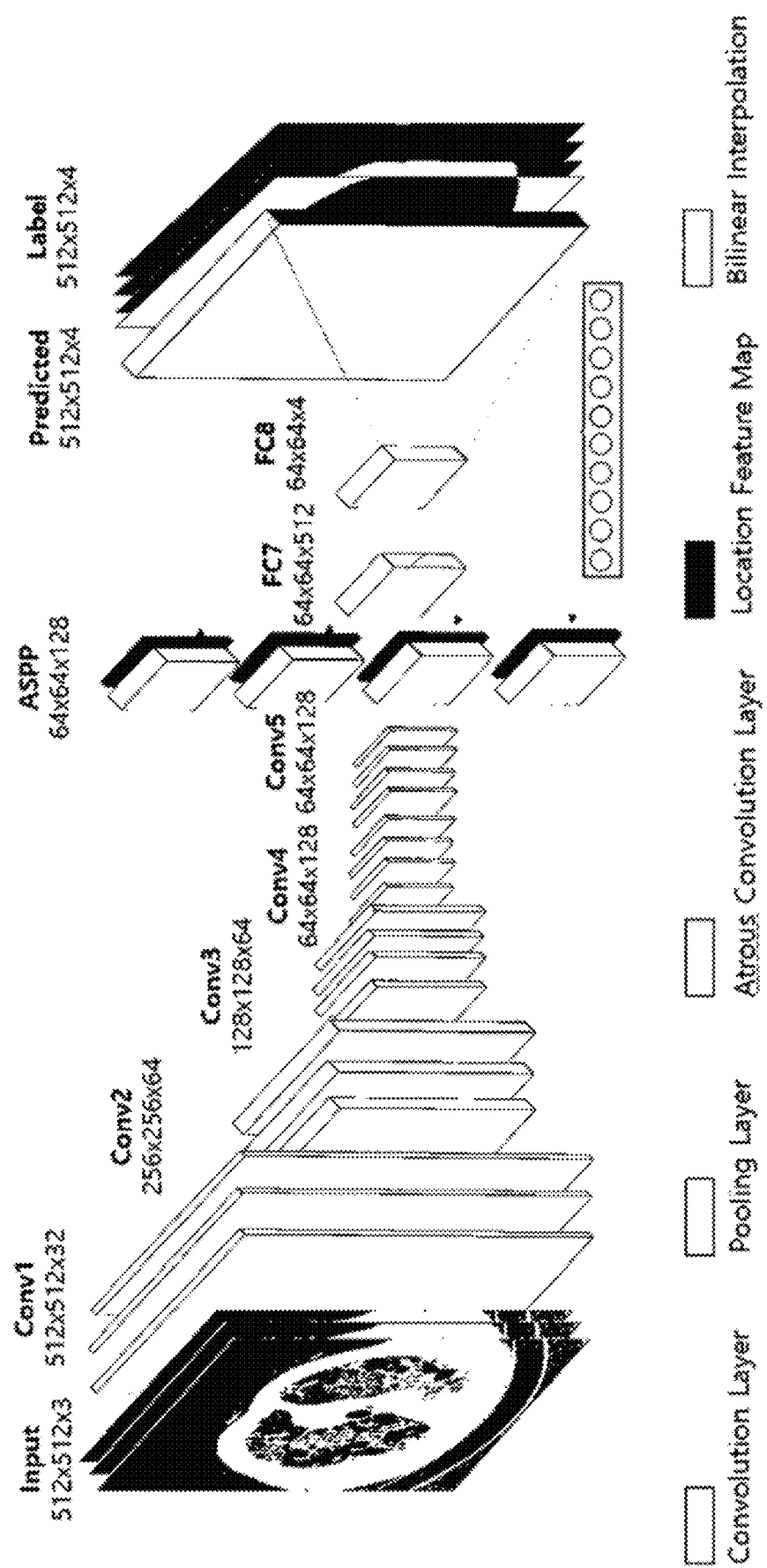

FIGS. 6A and 6B are views illustrating an example of a process of segmenting a specific region from a medical image according to the present disclosure, in which a lung CT image is used as the medical image 40 and a process of segmenting lung parenchyma from the medical image 40 is illustrated. U-Net may be used for segmentation, and various types of segmentation neural networks such as an FCN may also be used. However, in the case where only the individual image information is utilized in this way, assuming that the medical image 40 has p (p≥2) number of unit images which are numbered from 1 to k from the top with respect to an axial direction, the unit images located on a lower side may reflect the anatomical objects, rather than an analysis target such as the large intestine, to adversely affect the segmentation. Thus, in the process of training the segmentation module 50, location information may be given to the unit images located on the lower side, thereby solving the problem that segmentation is not properly performed due to such an anatomical object as the large intestine. Here, a method of assigning the location information may be a method of expressing coordinates of the corresponding unit image by a vector of a specific length on a whole axial space. For example, a 70th unit image, among all 100 unit images, may be expressed such that only 7th element in a vector having a 10-dimensional length has a value of 1 and the remaining elements have a value of 0. This may be provided as auxiliary input information to a hidden layer of the segmentation model 50 to improve the segmentation result.

Figure 7:
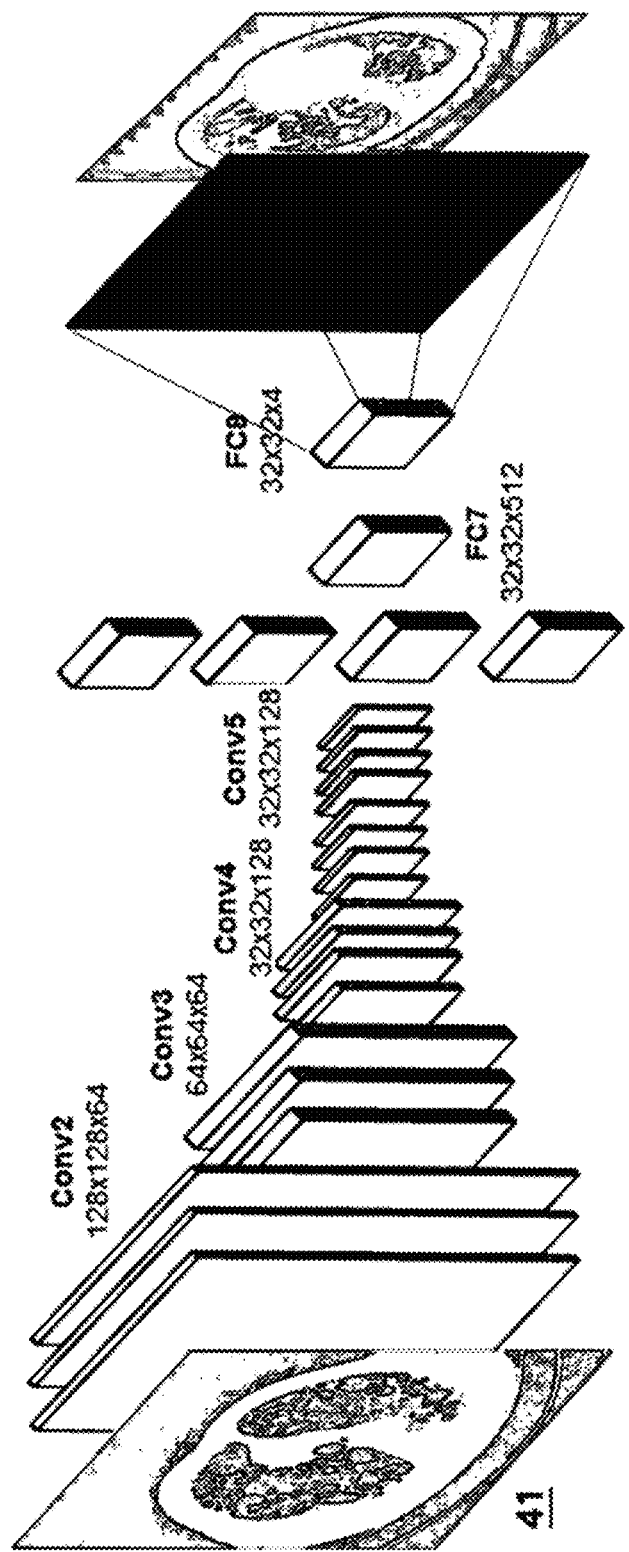
FIG. 7 is a diagram illustrating an example of a process of extracting features from a medical image according to the present disclosure.
Figure 8:
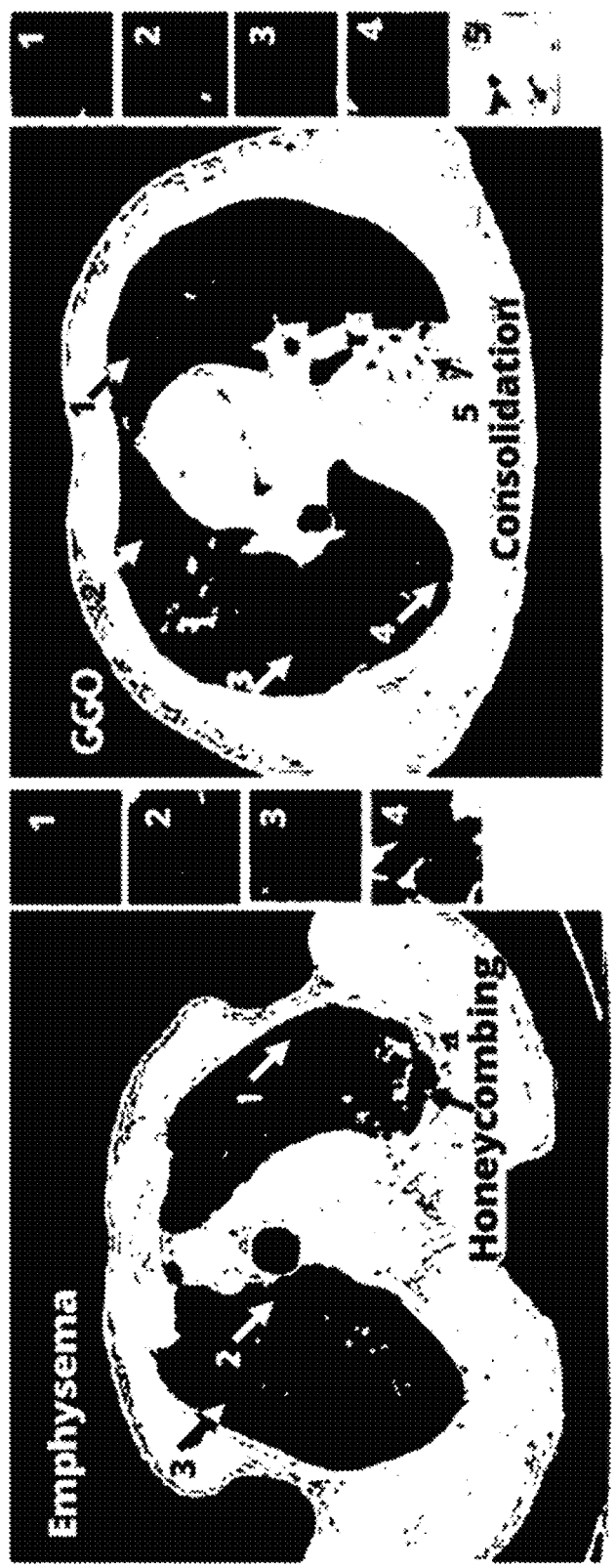
FIG. 8 is a view illustrating types of diffuse interstitial lung disease (DILD).

FIG. 7 is a diagram illustrating an example of a process of extracting features from a medical image according to the present disclosure, in which a process of evaluating whether or not a lung parenchyma 41 to be segmented in FIGS. 6A and 6B is of a diffuse interstitial lung disease is illustrated. For example, the feature extraction unit 60 may classify features into six types (Consolidation, Emphysema, Ground Glass Opacity, Honeycombing, Reticular Opacity, Normal; see FIG. 8) through feature extraction.

As in the segmentation, an artificial neural network such as FCN or U-Net and a classifier such as a soft-max function for type classification may be applied to feature extraction. When a target anatomical object region (e.g., lung parenchyma 41) is determined by the segmentation model 50 in the medical image 40, individual pixels in the corresponding anatomical object region are quantified by diseases (six disease types are classified in case of DILD). In this case, feature extraction may be a process of segmenting the corresponding region by diseases and quantifying each of the regions. That is, a quantized map having the same size as that of the input image may be generated (see the rightmost photograph in FIG. 7). Here, the status or the status value ($H_{\_ta}$ or $H_{\_tb}$) may be expressed as a vector of a specific length, and this may be a result of learning such that a similar image is represented by a similar vector based on a sequence of several quantized unit images. Further, here, the function $D(H_{\_ta}, H_{\_ta})$ is a similarity function, and any function may be used as long as it can compare distances between vectors having a specific length. For example, Euclidian distance, cosine similarity, or the like may be used. Meanwhile, it is possible to use a calculated value of the function $D(H_{\_ta}, H_{\_ta})$ in learning of the model. As illustrated in FIG. 5, a similarity between two medical image cases may be scored as (0, 1, 2, 3) and given as a learning label, and some (e.g., a parameter of the recurrent neural network 70) of parameters of the learning unit 31 and the user interface side output value processing unit 32 or the entire parameters of the model (a parameter of the segmentation module 50, a parameter of the feature extraction unit 60, and the parameter of the recurrent neural network 70) may be learned using the learning label.

Hereinafter, various embodiments of the present disclosure will be described.

(1) A content-based medical image retrieval method includes: obtaining m (2≤m≤n) number of unit images from a 3D medical image including n (n≥2) number of unit images and extracting features per unit image from each of the m (2≤m≤n) number of unit images; inputting each of features per unit image extracted from the m (2≤m≤n) number of unit images to a recurrent neural network to generate an output value; and performing medical image retrieval using the output value, wherein a plurality of three-dimensional (3D) medical images to be compared with the output value include a 3D medical image having p (p≥2, p≠n) number of unit images.

(2) The content-based medical image retrieval method may further include: segmenting a specific region regarding each of the m (2≤m≤n) number of unit images of the 3D medical image before the extracting features, wherein, in the extracting features, the features per unit image are extracted from the segmented specific region.

(3) In the content-based medical image retrieval method, location information indicating that an anatomical object which is not an analysis target is included is given to some of m (2≤m≤n) number of unit images.

(4) In the content-based medical image retrieval method, each of features per unit image are obtained through a process of segmenting a corresponding region by diseases and quantifying each of the segmented regions.

(5) In the content-based medical image retrieval method, a function of an output value generated for two 3D medical images represents similarity of the two 3D medical images, and the similarity is used for learning of a recurrent neural network.

(6) In the content-based medical image retrieval method, in the segmenting features, the specific region is of lung parenchyma, and in the extracting features, each of features per unit image are obtained through a process of segmenting the corresponding region by DILD diseases and quantifying each of the segmented regions.

(7) A content-based medical image retrieval system cooperating with a user interface and a medical image storage unit includes: a learning unit trained by a plurality of medical images provided from a medical image storage unit as training data; a user interface side output value processing unit for receiving the plurality of medical images and deriving an output value therefrom; and an input processing unit, as a storage space for storing the output value from the learning unit, for deriving at least one output value of the learning unit corresponding to an output value of the user interface side output value processing unit.

(8) In the content-based medical image retrieval system, the learning unit includes a feature extraction unit and a recurrent neural network.

(9) The content-based medical image retrieval system further includes: a segmentation module for segmenting a specific region of a medical image.

(10) In the content-based medical image retrieval system, the medical image includes a plurality of unit images, and the learning unit segments a specific region per unit image through the segmentation module, and allows the specific region per unit image to pass the feature extraction unit and the recurrent neural network to derive an output value therefrom, wherein the output value is used to retrieve a medical image of a case similar to a medical image.

While certain embodiments have been described, these embodiments have been presented by way of example only, and are not intended to limit the scope of the disclosures. Indeed, the embodiments described herein may be embodied in a variety of other forms. Furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A content-based medical image retrieval method, comprising:
    obtaining m (2≤m≤n) number of unit images from a three-dimensional (3D) current medical image including n (n≥2) number of unit images, wherein the 3D current medical image is in voxel data including a plurality of slices and each of the plurality of slices is defined as a unit image;
    extracting features from each of the obtained m number of unit images through a feature extraction unit by segmenting specific regions in each of the obtained m number of unit images by diseases and quantifying each of the segmented specific regions;
    inputting each of the features per unit image which are extracted from the m number of unit images to a neural network to generate a current output value, wherein the neural network is configured to derive the current output value using each of the features per unit image; and
    performing medical image retrieval using the current output value through an input processing unit,
    wherein a plurality of 3D reference medical images to be compared with the current output value include a 3D reference medical image having p (p≥2, p≠n) number of unit images,
    wherein the features from each of the obtained m number of unit images are classified based on type of the disease.

2. The method of claim 1, wherein location information indicating that an anatomical object which is not an analysis target is included is given to some of them (2≤m≤n) number of unit images.

3. The method of claim 1, wherein a function of an output value generated for two 3D medical images represents similarity of the two 3D medical images, and the similarity is used for learning of the neural network.

4. The method of claim 1,
    wherein the segmented specific regions from each of the obtained m number of unit images are lung parenchyma regions of a diffuse interstitial lung disease (DILD) disease, and
    wherein the features are classified based on a plurality of specific type of disease including a consolidation, an Ephysema, a ground glass opacity, a honeycombing, a reticular opacity and a normal.

5. The method of claim 1, wherein the neural network is a recurrent neural network (RNN) or a long short-term memory network (LSTM).

6. A content-based medical image retrieval system cooperating with a user interface and a medical image storage unit, comprising:
    a learning unit which is trained using a plurality of three-dimensional (3D) reference medical images provided from the medical image storage unit as training data, and receives each of the 3D reference medical images and derives a reference output value therefrom, and the learning unit includes a feature extraction unit for obtaining the plurality of unit images for each of the 3D reference medical images and extracting features per unit image from each of the unit images and a neural network for receiving the features per unit image to generate the reference output value for each of the 3D reference medical images, wherein the neural network is configured to derive the reference output value of each reference medical image using each of the features per unit image of the unit images constituting the reference medical image;

a user interface side output value processing unit for receiving m (2≤m≤n) number of unit images from a three-dimensional (3D) current medical image including n (n≥2) number of unit images provided from the user interface and configured to derive a current output value therefrom; and an input processing unit including a storage space for storing the plurality of reference output values generated from the learning unit, and configured to derive at least one reference output value of the learning unit corresponding to the current output value of the user interface side output value processing unit, wherein the learning unit further includes a segmentation module for segmenting specific regions of each reference medical image, wherein the learning unit segments specific regions by diseases per unit image through the segmentation module, and allows the specific regions per unit image to pass through the feature extraction unit and the neural network to derive the reference output value therefrom, wherein the plurality of 3D reference medical images and the current image are in voxel data including a plurality of slices and each of the plurality of slices is defined as a unit image, wherein the plurality of 3D reference medical images include a 3D medical image having p (p≥2, p≠n) number of unit images, wherein the extracting of the features from the segmented specific regions from each of the obtained m number of unit images through the feature extraction unit includes quantifying each of the segmented specific regions, wherein the features from each of the obtained m number of unit images are classified based on type of the disease.

7. The system of claim 6, wherein the neural network is a recurrent neural network (RNN) or a long short-term memory network (LSTM).

* * * * *

UNITED STATES PATENT AND TRADEMARK OFFICE
CERTIFICATE OF CORRECTION

PATENT NO. : 10,748,662 B2
APPLICATION NO. : 15/949537
DATED : August 18, 2020
INVENTOR(S) : Kyu Hwan Jung Page 1 of 1

It is certified that error appears in the above-identified patent and that said Letters Patent is hereby corrected as shown below:

On the Title Page

Item (30) Add the Foreign Application Priority Data as follows:
Country: KR (KOREA, REPUBLIC OF)
Priority No.: 10-2017-0109290
Priority Date: August 29, 2017

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*